(12) United States Patent
Simcock et al.

(10) Patent No.: US 9,921,151 B2
(45) Date of Patent: Mar. 20, 2018

(54) CORRECTION OF OPTICAL DEVICE THROUGHPUT ERRORS USING INTEGRATED COMPUTATIONAL ELEMENTS

(71) Applicant: Halliburton Energy Services, Inc., Houston, TX (US)

(72) Inventors: Michael N. Simcock, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/031,641

(22) PCT Filed: Dec. 19, 2013

(86) PCT No.: PCT/US2013/076635
§ 371 (c)(1),
(2) Date: Apr. 22, 2016

(87) PCT Pub. No.: WO2015/094297
PCT Pub. Date: Jun. 25, 2015

(65) Prior Publication Data
US 2016/0266033 A1    Sep. 15, 2016

(51) Int. Cl.
| G01N 21/25 | (2006.01) |
| G01N 21/31 | (2006.01) |
| G01J 3/28  | (2006.01) |
| G01J 3/32  | (2006.01) |
| G01N 21/65 | (2006.01) |
| G01N 21/64 | (2006.01) |
| G01J 3/12  | (2006.01) |

(52) U.S. Cl.
CPC ............ *G01N 21/31* (2013.01); *G01J 3/2803* (2013.01); *G01J 3/32* (2013.01); *G01N 21/255* (2013.01); *G01J 2003/1226* (2013.01); *G01N 21/65* (2013.01); *G01N 2021/3166* (2013.01); *G01N 2021/6471* (2013.01); *G01N 2201/127* (2013.01); *G01N 2201/1293* (2013.01)

(58) Field of Classification Search
CPC ...... G01N 21/31; G01N 21/65; G01N 21/255; G01N 2021/3166; G01N 2021/6471; G01N 2201/127; G01N 2201/1293; G01J 3/2803; G01J 3/32
USPC ....................................................... 356/416
See application file for complete search history.

(56) References Cited

U.S. PATENT DOCUMENTS 3,867,039 A * 2/1975 Nelson ...................... G01J 3/51
                                                    209/582
8,352,205 B2    1/2013 Myrick et al.
8,575,541 B1   11/2013 Jamison et al.
8,872,100 B1*  10/2014 Perkins .................. G01N 21/31
                                                    166/250.01

(Continued)

OTHER PUBLICATIONS

International Search Report and The Written Opinion of the International Search Authority, or the Declaration, dated Apr. 23, 2014, PCT/US2013/076635, 11 pages, ISA/US.

(Continued)

*Primary Examiner* — Hina F Ayub
(74) *Attorney, Agent, or Firm* — Haynes and Boone, LLP (57) ABSTRACT

An optical computing device utilizes an Integrated Computational Element ("ICE") core to correct calibration transfer errors in the device.

24 Claims, 5 Drawing Sheets

(56) References Cited

U.S. PATENT DOCUMENTS

| | | | | |
|---|---|---|---|---|
| 8,912,477 B2 * | 12/2014 | Freese | ............... | G01N 21/17 |
| | | | | 250/206 |
| 2006/0158734 A1 * | 7/2006 | Schuurmans | ............ | G01J 3/02 |
| | | | | 359/487.04 |
| 2009/0059226 A1 * | 3/2009 | Kajiki | ................. | G01J 3/02 |
| | | | | 356/328 |
| 2009/0216504 A1 | 8/2009 | Priore et al. | | |
| 2010/0027004 A1 * | 2/2010 | Bonyuet | ............... | G01J 3/02 |
| | | | | 356/326 |
| 2010/0042348 A1 * | 2/2010 | Bakker | ................ | G01J 3/28 |
| | | | | 702/85 |
| 2013/0284898 A1 | 10/2013 | Freese et al. | | |

OTHER PUBLICATIONS

Simcock, et al. "Precision in Imaging multivariate Optical Computing," Applied Optics, Mar. 1, 2007, vol. 46, Issue No. 7, pp. 1066-1089.

* cited by examiner

FIG. 6

CORRECTION OF OPTICAL DEVICE THROUGHPUT ERRORS USING INTEGRATED COMPUTATIONAL ELEMENTS

The present application is a U.S. National Stage patent application of International Patent Application No. PCT/US2013/076635, filed on Dec. 19, 2013, the benefit of which is claimed and the disclosure of which is incorporated herein by reference in its entirety.

FIELD OF THE DISCLOSURE

Embodiments of present disclosure generally relate to optical devices and, more particularly, to a multivariate optical computing device that utilizes Integrated Computational Element ("ICE") cores to correct device throughput errors.

BACKGROUND

ICE cores are variations of multivariate optical elements ("MOE") which were originally targeted for qualitative and quantitative analysis of physical or chemical properties of interest in chemometrics. In recent years, ICE technologies have been developed for various applications, including the Oil and Gas Industry in the form of optical sensors on downhole or surface equipment to evaluate a variety of fluid properties. ICE cores typically consist of multiple physical layers with different refractive indexes in the film material, wherein their optical or spectroscopic characteristics, if designed properly, can be transformed into effective inputs for linear and nonlinear multivariate calibration.

An optical computing device is a device configured to receive an input of electromagnetic radiation from a substance or sample of the substance and produce an output of electromagnetic radiation from a processing element. The processing element may be, for example, an ICE core. Fundamentally, optical computing devices utilize optical cores to perform regression calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." Thus, the optical computing device, through use of the ICE core, is capable of extracting the information of the spectral fingerprint of multiple characteristics or analytes within a substance and converting that information into a detectable output regarding the overall properties of a sample.

Optical computing devices are often characterized in terms of each of their optical components. The total system throughput can be estimated as the product of these components, with each component imposing its individual effect on the spectral throughput of the device. However, the spectral throughput of compiled optical systems often differ from the modeled spectral throughput due to a number of factors, such as lens aberrations, variation in optical elements, variation in optical element position, and other random errors, all of which are not accounted for in the model. In addition, systematic errors (in which there is a constant error in the spectral profile) are also unaccounted for in the model. As a result, the assembled optical computing device will contain throughput errors which may result in performance degradation in prediction of sample characteristics.

Accordingly, there is a need in the art for methods by which to correct for throughput errors in optical systems.

DESCRIPTION OF ILLUSTRATIVE EMBODIMENTS

Illustrative embodiments and related methods of the present disclosure are described below as they might be employed in an optical computing device that self-corrects system throughput errors. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, embodiments of the present disclosure are directed to an optical computing device which utilizes an Integrated Computation Element ("ICE") core to correct for system throughput errors, referred to herein as calibration transfer errors ("CTEs"). In a generalized method, the CTE of the optical computing device is determined based upon the device components. Using the CTE, a correction to the CTE ("CTE correction") is determined and then utilized to design an ICE core having the spectral profile necessary to correct for CTEs. In a generalized embodiment of the present disclosure, the optical computing device includes a first ICE core and a second error correcting ICE core. The first ICE core functions to determine the sample characteristic as understood in the art. However, the second ICE core acts to correct for CTEs introduced by the device components in a variety of ways. In a first embodiment, the second ICE core itself corrects the electromagnetic output of the first ICE core. In a second embodiment, an error correcting circuit utilizes detector output signals corresponding to the first and second ICE cores to correct for CTEs. In a third embodiment, a computer processor analyzes those same detector output signals to correct for CTEs. Accordingly, embodiments of the present disclosure provide an optical computing device that self-corrects for throughput errors which were not accounted-for during the design process.

Figure 1:
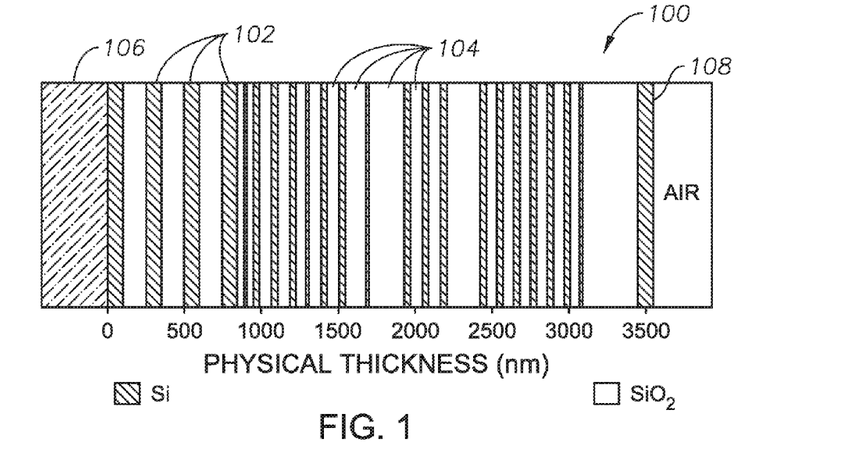
FIG. 1 shows an illustrative ICE core which may be fabricated using methods of the present disclosure.

As will be described in more detail below, the CTE correcting ICE core is designed to have a spectral profile (i.e., transmission function) which corrects the CTE. This is achieved, in part, varying the thickness of the layers forming the CTE correcting ICE core. To generally illustrate this point, FIG. 1 shows an illustrative ICE core 100 which may be fabricated using methods of the present disclosure. ICE core 100 may include a plurality of alternating layers 102 and 104, such as, for example, silicon (Si) and quartz ($SiO_2$), respectively. Other non-limiting examples of layer material include niobium, germanium and Germania, MgF, SiO, and other high and low index materials, although persons of ordinary skill in the art having the benefit of this disclosure will understand that these layers consist of materials whose index of refraction is high and low, respectively.

The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethylmethacrylate PMMA), polyvinylchloride (PVC), diamond, ceramics, etc., as known in the art. At the opposite end (e.g., opposite the optical substrate 106), the ICE core 100 may include a layer 108 that is generally exposed to the environmental air surrounding the device or installation. The number of layers 102, 104 and the thickness of each layer 102, 104 may be determined from the spectral attributes acquired from a spectroscopic analysis of a characteristic of the sample substance using a conventional spectroscopic instrument.

The spectrum of interest of a given characteristic of a sample typically includes any number of different wavelengths. It should be understood that the illustrative ICE core 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered to limit the present disclosure. Moreover, those skilled in the art will readily recognize that the materials that make up each layer 102, 104 may vary, depending on the application, cost of materials, and/or applicability of the material to the sample substance. For example, the layers 102, 104 may be made of, but are not limited to, silicon, quartz, germanium, water, combinations thereof, or other materials of interest. Furthermore, those same skilled persons will realize that the physical thicknesses of the layers 102 are illustrative in nature and, thus, may be altered as desired.

The multiple layers 102, 104 exhibit different refractive indices. By properly selecting the materials of the layers 102, 104 and their relative thicknesses and spacing, the illustrative ICE core 100 may be configured to selectively pass/reflect/refract predetermined fractions of light (i.e., electromagnetic radiation) at different wavelengths. Through the use of regression techniques, the corresponding output light intensity of the ICE core 100 conveys information regarding a characteristic of the analyte of interest. Moreover, as will be described below, through proper selection of the layer thicknesses, an ICE core may be designed to correct for CTEs in the compiled optical computing device.

Figure 2A:
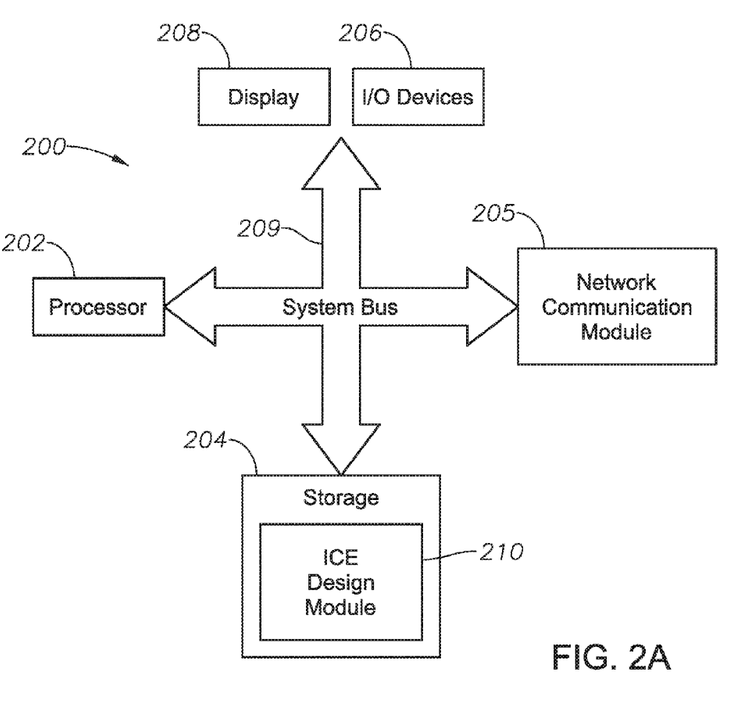
FIG. 2A shows a block diagram of an ICE design system according to an illustrative embodiment of the present disclosure.
Figure 2B:
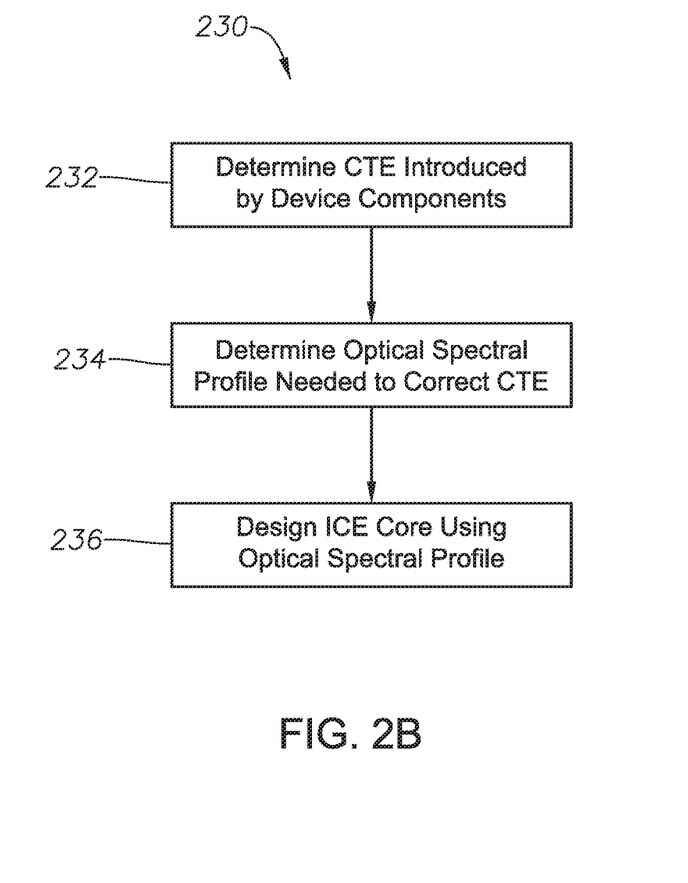
FIG. 2B is a flow chart of a illustrative method performed by the ICE design system to determine the design of an ICE core to correct a calibration transfer error.

In view of the foregoing, FIG. 2A shows a block diagram of an ICE design system according to an illustrative embodiment of the present disclosure. As will be described herein, ICE design system 200 provides a platform for the design of ICE cores which correct for CTEs. FIG. 2B is a flow chart of an illustrative method 230 performed by ICE design system 200 to determine the design of the CTE correcting ICE core. As will be described in more detail below, at block 232, ICE design system 200 analyzes an optical computing device (assembled or non-assembled) in order to determine the device throughput errors (i.e., CTE) introduced by the device components. The device components may include, for example, the lens, beam splitters, or other optical elements along the optical train. Once determined, at block 234, the system then determines the optical spectral profile (regression vector, for example) necessary to correct for the CTE. Based upon this optical spectral profile, at block 236, system 200 then determines the design of an ICE core having the appropriate spectral profile to correct for the CTE.

Still referring to FIG. 2A, ICE design system 200 includes at least one processor 202, a non-transitory, computer-readable storage 204, transceiver/network communication module 205, optional I/O devices 206, and an optional display 208 (e.g., user interface), all interconnected via a system bus 209. In one embodiment, the network communication module 205 is a network interface card and communicates using the Ethernet protocol. In other embodiment, the network communication module 105 may be another type of communication interface such as a fiber optic interface and may communicate using a number of different communication protocols. Software instructions executable by the processor 202 for implementing software instructions stored within ICE design module 210 in accordance with the illustrative embodiments described herein, may be stored in storage 204 or some other computer-readable medium.

Although not explicitly shown in FIG. 2A, it will be recognized that ICE design system 200 may be connected to one or more public (e.g., the Internet) and/or private networks via one or more appropriate network connections. It will also be recognized that the software instructions comprising ICE design module 210 may also be loaded into storage 204 from a CD-ROM or other appropriate storage media via wired or wireless methods.

Moreover, those skilled in the art will appreciate that embodiments of the present disclosure may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present disclosure. Embodiments of the disclosure may be practiced in distributed-computing environments where tasks are performed by remote-processing devices that are linked through a communications network. In a distributed-computing environment, program modules may be located in both local and remote computer-storage media including memory storage devices. Embodiments of the present disclosure may therefore, be implemented in connection with various hardware, software or a combination thereof in a computer system or other processing system.

An illustrative methodology by which ICE design system 200 determines the design of an ICE core will now be described. In multivariate calibration for spectral analysis, a regression vector r is determined, which can be combined with spectra to provide an estimate of the property/characteristic of interest ($\hat{y}$) as shown in Equation 1 below. Typically, $\hat{y}$ (the predicted characteristic of interest) will not completely replicate y (the actual characteristic of interest); consequently, there will be a chemometric error ("CHE"). In Equation 1 below, the rows represent the spectra (s1=spectra 1), the columns are the wavelength channels ($\lambda$2=wavelength channel 2), and r is the regression vector (r3=the value of the regression vector for wavelength channel 3). $\hat{y}$ is the column vector of predicted values for the characteristic of interest, as determined from each of the spectra.

$$\begin{bmatrix} s1\lambda1 & s1\lambda2 & s1\lambda3 & \ldots & s1\lambda x \\ s2\lambda1 & s2\lambda2 & s2\lambda3 & \ldots & s2\lambda x \\ s3\lambda1 & s3\lambda2 & s3\lambda3 & \ldots & s3\lambda x \\ \ldots & \ldots & \ldots & \ldots & \ldots \\ sz\lambda1 & sz\lambda x & sz\lambda1 & \ldots & sy\lambda x \end{bmatrix} \cdot \begin{bmatrix} r_1 \\ r_2 \\ r_3 \\ \ldots \\ r_x \end{bmatrix} = \hat{y}. \quad \text{Eq. (1)}$$

In multivariate optical computing ("MOC"), several components are characterized separately and assembled to produce the final optical computing device. Because of this process, system throughput errors may exist as a result of alignment, variations in the angles of incidence, and deviations in detectors, light sources, or other optical components. These system throughput errors are not sample spectra errors, and can be referred to as "fixed modification" of the system throughput. The fixed modification to the spectral throughput of the system may deteriorate the accuracy of the device in determining the sample characteristics.

This fixed modification to the spectral throughput can be called a calibration transfer error, or CTE as previously discussed. This CTE is imposed equally on each sample spectra detected by the optical computing device. This is represented in the left side of Equation 2 below as the variable m, a function of wavelength (e.g., m2=CTE modification at wavelength channel 2). With this modified dataset, the original prediction vector $\hat{y}$ will be affected to instead provide other, inevitably less accurate, prediction values which are referred to herein as the system response $\hat{y}'$.

$$\begin{bmatrix} s1\lambda1m1 & s1\lambda2m2 & s1\lambda3m3 & \ldots & s1\lambda xmx \\ s2\lambda1m1 & s2\lambda2m2 & s2\lambda3m3 & \ldots & s2\lambda xmx \\ s3\lambda1m1 & s3\lambda2m2 & s3\lambda3m3 & \ldots & s3\lambda xmx \\ \ldots & \ldots & \ldots & \ldots & \ldots \\ sz\lambda1m1 & sz\lambda2m2 & sz\lambda3m3 & \ldots & sy\lambda xmx \end{bmatrix} \cdot \begin{bmatrix} r1 \\ r2 \\ r3 \\ \ldots \\ rx \end{bmatrix} = \hat{y}'. \quad \text{Eq. (2)}$$

Equation 2 can be rearranged to contain a known n×p matrix and the unknown m vector. The n×p matrix in this optical computing device essentially contains all of the $\hat{y}$ information regarding what the predicted characteristic value should have been, were it not for the CTE (m) vector. The value $\hat{y}'$ is a measured response of the device with the unknown CTE error vector. From this Equation 2, a series of measurements must be made with the assembled device (with CTE) using reference solutions that are identical to the original solutions used to make the calibration data. Then, the actual system response to these solutions must be measured. Because Equation 2 is of the same form as a typical chemometric problem, m can be solved by standard partial least squares ("PLS") analysis as in Equation 3 below.

$$\begin{bmatrix} s1\lambda1r1 & s1\lambda2r2 & s1\lambda3r3 & \ldots & s1\lambda xrx \\ s2\lambda1r1 & s2\lambda2r2 & s2\lambda3r3 & \ldots & s2\lambda xrx \\ s3\lambda1r1 & s3\lambda2r2 & s3\lambda3r3 & \ldots & s3\lambda xrx \\ \ldots & \ldots & \ldots & \ldots & \ldots \\ sz\lambda1r1 & sz\lambda2r2 & sz\lambda3r3 & \ldots & sy\lambda xrx \end{bmatrix} \cdot \begin{bmatrix} m1 \\ m2 \\ m3 \\ \ldots \\ mx \end{bmatrix} = \hat{y}'. \quad \text{Eq. (3)}$$

After the CTE vector has been determined, system 200 may then use it to modify the original regression vector to enable the original value of $\hat{y}$ to be recovered. This is shown in Equation 4 below, in which the n×p matrix is actually measured containing the error, and this error can be cancelled by modifying the regression vector. If any m value is zero, then the information in that wavelength channel will be lost, which may affect the predictability of the whole optical computing device. However, it will be noted that the expected values of m will greater than zero and should be close to one when there is no CTE. The bandwidth of the measurement is most important in retaining $\hat{y}$, regardless of the CTE shape; $\hat{y}$ can be recovered exactly and the predictability standard error of prediction ("SEP") will remain the same, as long as m has no zero points. Sensitivity, however, can be affected as will be understood by those ordinarily skilled in the art having the benefit of this disclosure.

$$\begin{bmatrix} s1\lambda1m1 & s1\lambda2m2 & s1\lambda3m3 & \ldots & s1\lambda xmx \\ s2\lambda1m1 & s2\lambda2m2 & s2\lambda3m3 & \ldots & s2\lambda xmx \\ s3\lambda1m1 & s3\lambda2m2 & s3\lambda3m3 & \ldots & s3\lambda xmx \\ \ldots & \ldots & \ldots & \ldots & \ldots \\ sz\lambda1m1 & sz\lambda2m2 & sz\lambda3m3 & \ldots & sy\lambda xmx \end{bmatrix} \cdot \begin{bmatrix} r1/m1 \\ r2/m2 \\ r3/m3 \\ \ldots \\ rx/mx \end{bmatrix} = \hat{y}. \quad \text{Eq. (4)}$$

With the foregoing fundamental understanding, it will now be described how illustrative embodiments of ICE design system 200 determines the design of an ICE core to correct the CTE of an optical computing device. Note that the analogous calculation used in MOC varies slightly from Equations 1-4 in that the regression vector is fixed in an ICE core. As a result, the spectral modification m must be implemented by a spectral correction ICE core (i.e., CTE correcting ICE core) placed in the beam path, which will produce a spectral transmission throughput correction on the device spectral profile. Because, with MOC, the signal is typically a ratio of the intensity with and without the ICE core, the CTE is applied to the background and ICE signals separately. As a result, Equations 1-4 4 must be modified slightly, although the underlying principle for determining m is the same.

Figure 3:
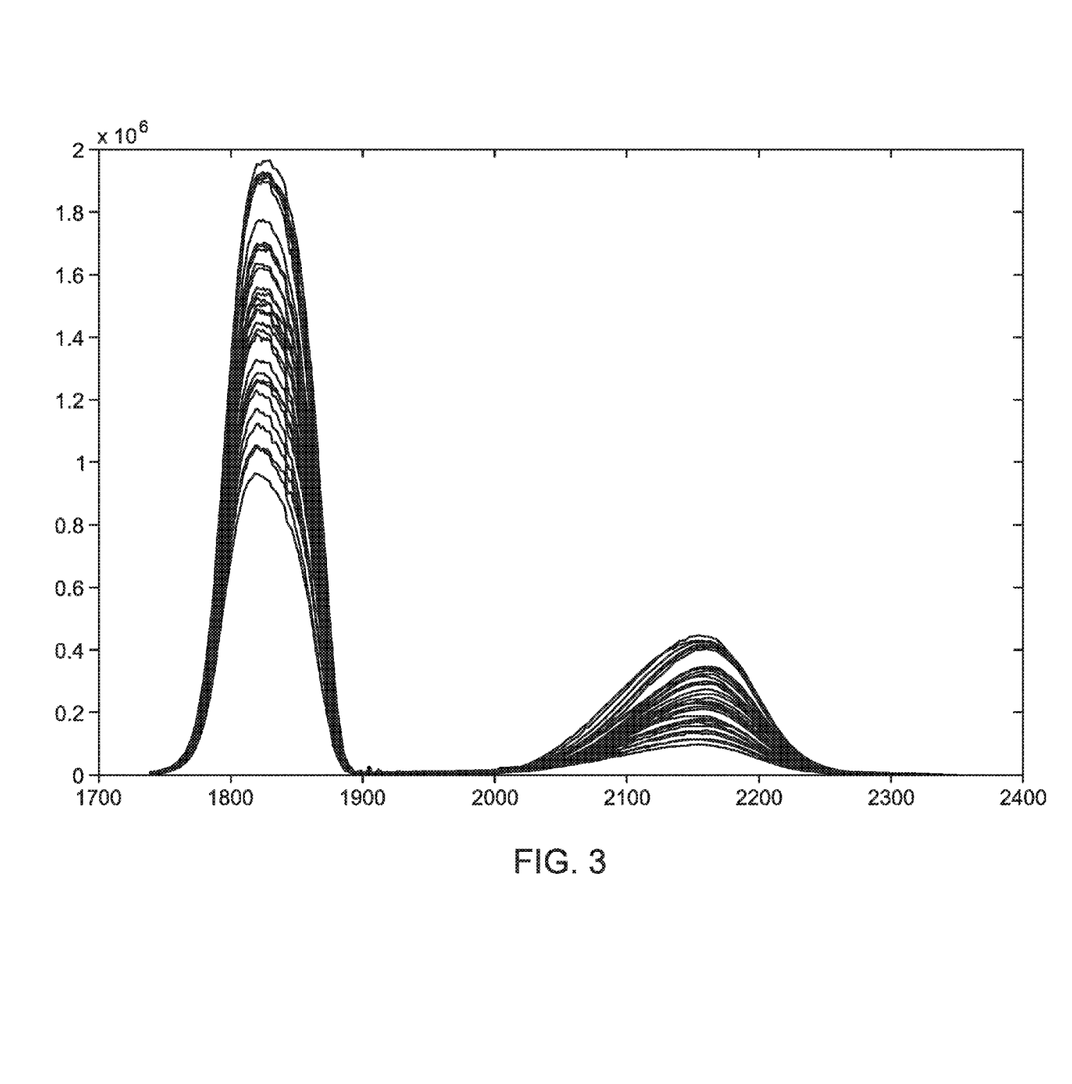
FIG. 3 is a graph of combined and normalized raw spectral data and device spectral throughput data utilized to design the ICE core to correct the calibration transfer error.

To begin an illustrative analysis, ICE design system 200 may combine the raw spectral data with the device spectral throughput, as shown in FIG. 3. FIG. 3 shows the original, normalized data with bandpass plotted along the $X_{axis}$ (wavelength (nm)) and $Y_{axis}$ (normalized intensity). The convolved data (spectra and system responses) is normalized to total intensity, then a regression vector using PLS is determined by system 200. Applying the regression vector to the convolved spectra will give ŷ, the expected (most accurate) predicted concentrations. If CTE is present, ŷ contains more error than would be expected (less accurate). The discrepancy between the expected (most accurate) predicted characteristic of interest and the less accurate characteristic of interest can then be used by system 200 to calculate the original transfer error, as described above.

In some cases, the solution to Equation 3 can be underdetermined, depending on the number of samples available and the number of measurements made. This problem may be addressed in two ways. First, for example, if there are several analytes, several regression vectors may be made available (for MOC, this corresponds to an optical computing device with several ICE cores). The samples plotted in FIG. 3 contains four analytes: water, NaOH, $Na_2CO_3$, and NaCl. Using these four regression vectors combined with the 34 sets of spectral data shown in FIG. 3 enables 132 combinations on which to calculate the CTE. In MOC, four sets of ŷ' can be measured if four ICE cores are designed, thus increasing the amount of data with which to determine the CTE. Alternatively, the second method of determining CTE in underdetermined systems is to reduce the resolution of m, and thus the number of parameters to fit. An example is to use a Fourier transform interpolation function to change the resolution of m.

Figure 4:
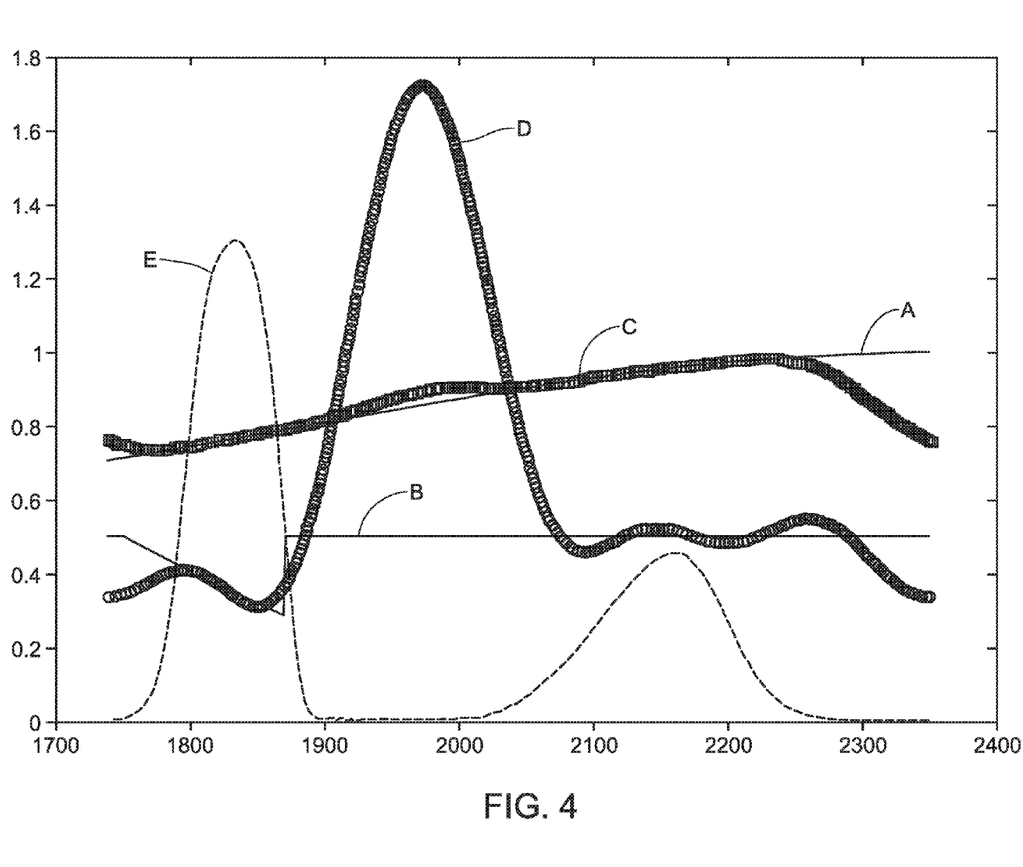
FIG. 4 is a graph showing two examples of simulated calibration transfer error profiles (shown by lines A and B), and the back-calculated versions of the function (shown by lines C and D) that are based on a Fourier transform interpolation of eight points, all generated using the ICE design system 200.

FIG. 4 provides two examples of simulated CTE profiles (shown by lines A and B), and the back-calculated versions of the function (shown by lines C and D) that are based on a Fourier transform interpolation of eight points, all generated using ICE design system 200. Line E indicates the standard deviation ("SD") of the spectral data from FIG. 3 and shows the wavelengths in which the sample does not transmit (SD values of near zero). With the back-calculated CTE profiles, it is evident that in the regions in which there is no transmission, the CTE is more poorly recreated; in the regions in which the SD is high, the CTE Is quite closely replicated. Line A illustrates the first function replicated; the slight curve of this function reflects the type of CTE expected. It is replicated well when the SD of the raw data is significantly above zero. The second CTE function has a sharp transit. Although it is not identical to the original CTE and is rather unrealistic, it is still reasonably replicated and can compensate very well for the prediction error. The slopes and curves are back-calculated well using this method; predictabilities are compensated well, even when deviations exist from the original CTE.

Accordingly, in certain illustrative embodiments of the present disclosure, ICE design system 200 utilizes the foregoing methodology to design an ICE core to compensate for the CTE. The resulting ICE core(s) are design to have the appropriate spectral profile to produces an m value that corrects ŷ' back to ŷ, or alternative embodiments, closer to the actual values, y, where y'>ŷ>y. To achieve this in one embodiment, ICE design system 200 defines m as the transmission profile of an optical filter (i.e., ICE core), constrained as it is with one or more thin film layers with the possibility to vary the layer thicknesses (as discussed above in relation to FIG. 1). The thickness of layer(s) 102, and layer(s) 104 are then adjusted to produce a correction profile, m, that results in a spectral profile throughput modification that provides a greater accuracy level for the predicted characteristic of interest. In other words, system 200 designs an ICE core that applies a calibration transfer error correction, or CTE correction, to the output of the optical computing device.

Figure 5:
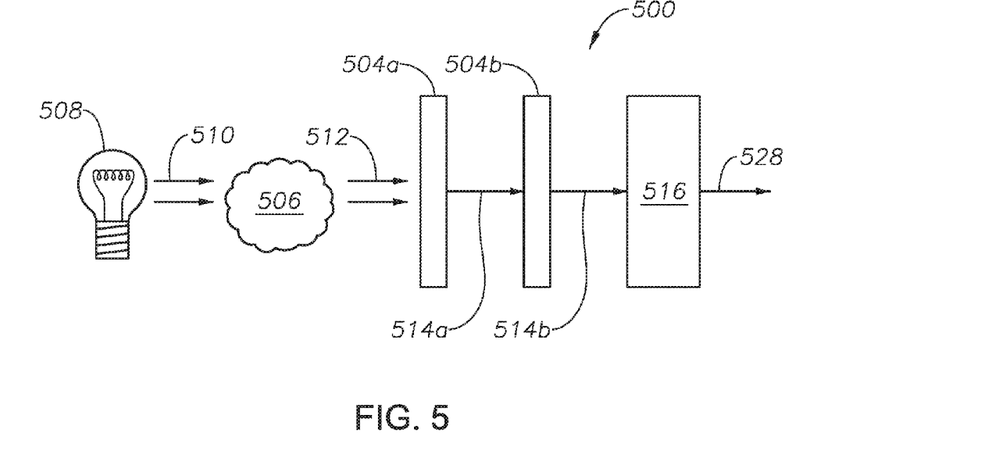
FIG. 5 is a block diagram of an illustrative architecture of an optical computing device employing a transmission mode design, which may be utilized in one or more of the optical computing devices of the present disclosure.

FIG. 5 is a block diagram of an illustrative architecture of an optical computing device 500 employing a transmission mode design, which may be utilized in one or more of the optical computing devices of the present disclosure. As will be described, optical computing device 500 corrects the CTE optically using an ICE core. An electromagnetic radiation source 508 may be configured to emit or otherwise generate electromagnetic radiation 510. As understood in the art, electromagnetic radiation source 508 may be any device capable of emitting or generating electromagnetic radiation. For example, electromagnetic radiation source 508 may be a light bulb, light emitting device, laser, blackbody, photonic crystal, or X-Ray source, natural luminescence, etc. In one embodiment, electromagnetic radiation 510 may be configured to optically interact with the sample 506 to thereby generate sample-interacted light 512. Sample 506 may be any desired sample, such as, for example, a fluid (liquid or gas), solid substance or material such as, for example, hydrocarbons or food products. While FIG. 5 shows electromagnetic radiation 510 as passing through or incident upon the sample 506 to produce sample-interacted light 512 (i.e., transmission or fluorescent mode), it is also contemplated herein to reflect electromagnetic radiation 510 off of the sample 506 (i.e., reflectance mode), such as in the case of a sample 506 that is translucent, opaque, or solid, and equally generate the sample-interacted light 512.

After being illuminated with electromagnetic radiation 510, sample 506 containing an analyte of interest (a characteristic of the sample) produces an output of electromagnetic radiation (sample-interacted light 512, for example). As previously described, sample-interacted light 512 also contains spectral information of the sample used to determine one or more characteristics of sample 506. Although not specifically shown, one or more spectral elements may be employed in optical computing device 500 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Although not shown, optical computing device 500 may be coupled to a remote power supply, while in other embodiments optical computing device 500 comprises an on-board battery. Optical computing device 500 may also comprise a signal processor (not shown), communications module (not shown) and other circuitry necessary to achieve the objectives of the present disclosure, as will be understood by those ordinarily skilled in the art having the benefit of this disclosure. It will also be recognized that the software instructions necessary to carry out the objectives of the present disclosure may be stored within storage located on optical computing device 500 or loaded into that storage from a CD-ROM or other appropriate storage media via wired or wireless methods.

Alternatively, however, the processor may be located remotely from optical computing device 500. In such embodiments, a communications link provides a medium of communication between the processor and optical computing device 500. The communications link may be a wired link, such as, for example, a fiber optic cable. Alternatively, however, the link may be a wireless link. In certain illustrative embodiments, the signal processor controls operation of optical computing device 500. Optical computing device 500 may also include a transmitter and receiver (transceiver, for example) (not shown) that allows bi-directional communication over a communications link in real-time. In certain illustrative embodiments, optical computing device 500 will transmit all or a portion of the sample characteristic data to a remote processor for further analysis. However, in other embodiments, such analysis is completely handled by optical computing device 500 and the resulting data is then transmitted remotely for storage or subsequent analysis. In either embodiment, the processor handling the computations may, for example, analyze the characteristic data, or perform simulations based upon the characteristic data, as will be readily understood by those ordinarily skilled in the art having the benefit of this disclosure.

Still referring to the illustrative embodiment of FIG. 5, sample-interacted light 512 is then directed to a first ICE core 504a, which has been designed to be associated with a particular characteristic of sample 506 or may be designed to approximate or mimic the regression vector of the characteristic in a desired manner, as would be understood by those ordinarily skilled in the art having the benefit of this disclosure. Additionally, however, optical computing device 500 also includes a second ICE core 504b which is designed to correct the CTE, as previously described. Second ICE core 504b is positioned in series with first ICE core 504a. Also, as previously described, ICE cores 504a and 504b have different spectral profiles and, as a result, second ICE core 504b itself corrects the CTE present in optical computing device 500.

When sample-interacted light 512 optically interacts with first ICE core 504a, a first electromagnetic beam 514a is generated which, as previously described, may contain the less accurate device response 9'. First electromagnetic beam 514a then optically interacts with second ICE core 504b to thereby produce second electromagnetic beam 514b. Since second ICE core 504b contains the appropriate spectral profile that produces the m value, $\hat{y}'$ is corrected back to $\hat{y}$, closer to the actual values, y, where $y'>\hat{y}>y$, thus providing a CTE correction to the beam. Thereafter, second electromagnetic beam 514b, which is now correctly related to the characteristic or analyte of interest, is conveyed to a series detector 516 for analysis and quantification. Note, however, that in an alternative embodiment, the CTE correcting ICE core may be ICE core 504a, while ICE core 504b would include the conventional design.

Detector 516 may be any device capable of detecting electromagnetic radiation, and may be generally characterized as an optical transducer. For example, detector 516 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art. Detector 516 is further configured to produce an output signal 528 in the form of a voltage that corresponds to the characteristic of the sample 506. In at least one embodiment, output signal 528 produced by detector 516 and the characteristic concentration of the sample 506 may be directly proportional. In other embodiments, the relationship may be a polynomial function, an exponential function, and/or a logarithmic function.

Although not shown, optical computing device 500 may include a second detector arranged to receive and detect electromagnetic radiation (sample-interacted light 512) and output a normalizing signal, as understood in the art. Here, reflected electromagnetic radiation may include a variety of radiating deviations stemming from electromagnetic radiation source 508 such as, for example, intensity fluctuations in the electromagnetic radiation, interferent fluctuations (for example, dust or other interferents passing in front of the electromagnetic radiation source), combinations thereof, or the like. Thus, the second detector detects such radiating deviations as well.

Although not shown in FIG. 5, in certain illustrative embodiments, detector 516 may be communicably coupled to a signal processor (not shown) on-board optical computing device 500 such that a normalizing signal indicative of electromagnetic radiating deviations may be provided or otherwise conveyed thereto. The signal processor may then be configured to computationally combine the normalizing signal with output signal 528 to provide a more accurate determination of the characteristic of sample 506. However, in other embodiments that utilized only one detector as shown, the signal processor would be coupled to the one detector. Nevertheless, in the embodiment of FIG. 5, for example, the signal processor may utilize multivariate analysis techniques such as, for example, standard partial least squares ("PLS") which are available in most statistical analysis software packages (for example, XL Stat for MICROSOFT® EXCEL® the UNSCRAMBLER® from CAMO Software and MATLAB® from MATHWORKS®), as will be understood by those ordinarily skilled in the art having the benefit of this disclosure. Thereafter, the resulting data is then transmitted to the processor for further operations.

Figure 6:
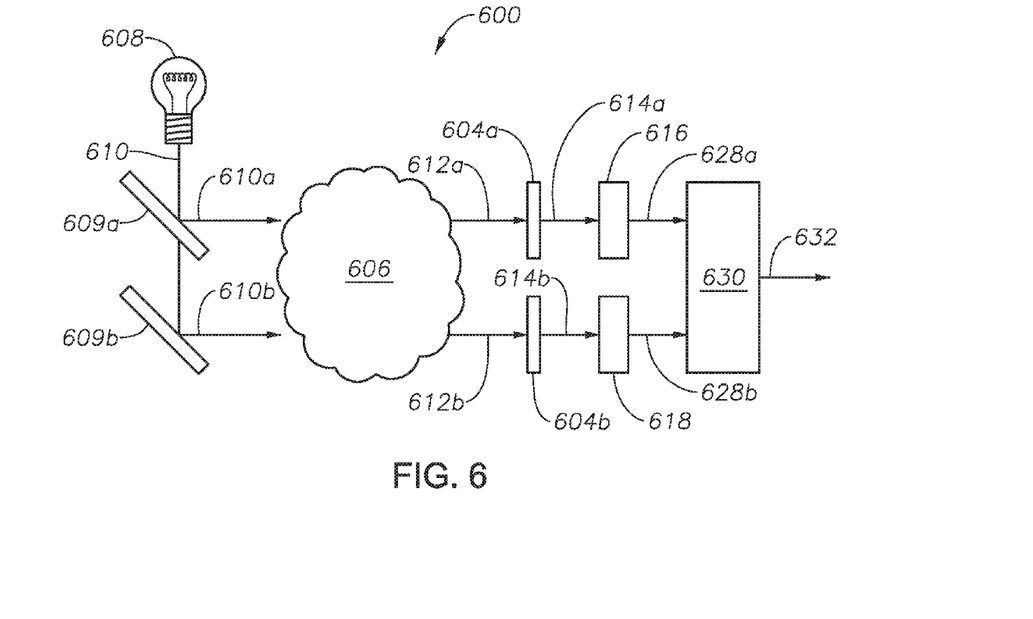
FIG. 6 is a block diagram of an illustrative architecture of an optical computing device utilizing a calibration transfer error correction circuit, according to certain illustrative embodiments of the present disclosure.

FIG. 6 is a block diagram of an illustrative architecture of an optical computing device 600 utilizing a CTE error correction circuit, according to certain illustrative embodiments of the present disclosure. As will be described, optical computing device 600 corrects the CTE electronically using the correction circuit. An electromagnetic radiation source 608 generates electromagnetic radiation 610, which is then split into two beams 610a and 610b using beam splitters and/or reflectors 609a and 609b, as understood in the art. Electromagnetic radiation beams 610a,b then optically interact with sample 606 to produce sample-interacted light 612a,b, respectively. A first ICE core 604a and a second ICE core 604b are positioned in parallel configuration to receive sample-interacted light 612a,b, respectively, and thereby produce first electromagnetic beam 614a and second electromagnetic beam 614b. In this example, second ICE core 604b serves as the CTE correcting ICE core; however, in alternate embodiments, first ICE core 604a may serve as the CTE correcting ICE core as previously described.

A first detector 616 is positioned in series with first ICE core 604a to thereby optically interact with first electromagnetic beam 614a to produce first signal 628 which corresponds to a desired characteristic of sample 606. A second detector 618 is positioned in series with second ICE core 604b to optically interact with second electromagnetic beam 614b which contains the transmission function necessary to produce the correcting m value. This interaction results in the production of second signal 628b.

Both the first and second signals 628a,b are utilized to determine the characteristic of sample 606, as one of the signals (in this example, second sign 628b) is used to apply a CTE correction to the other signal. In this illustrative embodiment, a CTE correction circuit 630 applies the CTE correction of second signal 628b to first signal 628a. There are a variety of ways in which to design circuit 630. For example, circuit 630 may be a differential op-amp circuit coupled to detectors 616 and 618 to thereby subtract signal 628*b* from signal 628*a*. Alternatively, however, other math operators may be design into circuit 630, as would be understood by those ordinarily skilled in the art having the benefit of this disclosure. Nevertheless, the resulting output signal 632 corresponds to the CTE corrected characteristic, and is ultimately processed accordingly by a remote or locate processor (not shown).

In an alternate embodiment of optical computing device 600, a computer processor (not shown) may be utilized instead of CTE correction circuit 630. In such an embodiment, correction of the CTE (using signals 628*a,b*) would be performed by the computer processor via software instructions. For example, the software instructions would enable the computer processor to subtract second signal 628*b* from first signal 628*a* to thereby determine the CTE corrected characteristic of sample 606.

In yet another alternative embodiment, the conventional ICE core and the CTE corrective ICE core may be one monolithic device. For example, one of the ICE cores may be deposited onto (or attached to) one side of a substrate, while the other ICE core is attached to, or deposited onto), the opposite side of the substrate. Such an alteration would be apparent to one ordinarily skilled in the art having the benefit of this disclosure.

Those same ordinarily skilled persons will realize the aforementioned optical computing devices are illustrative in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). The foregoing optical computing devices may be implemented in a variety of ways, including, for example, in a downhole environment, compact device, hand-held devices or other portable devices.

Accordingly, the illustrative embodiments of the present disclosure provide for the design and fabrication of ICE cores that can compensate for the error in an assembled optical computing device's spectral profile. As a result, the integrity of the optical device's performance is maintained even when unaccounted-for errors in the modeling process are present. As a result, there is no need to recollect spectral data in order to compensate for the errors.

Embodiments described herein further relate to any one or more of the following paragraphs:

1. An optical computing device, comprising electromagnetic radiation that optically interacts with a sample to produce sample-interacted light; a first Integrated Computational Element ("ICE") core; a second ICE core positioned in series with the first ICE core; and a detector positioned in series with the first and second ICE cores to receive an electromagnetic beam which has passed through the first and second ICE cores, the detector thereby generates a signal utilized to determine a characteristic of the sample.

2. An optical computing device as defined in paragraph 1, wherein the first and second ICE cores have different spectral profiles.

3. An optical computing device as defined in any of paragraphs 1-2, wherein the first or second ICE cores are positioned to apply a calibration transfer error correction to the electromagnetic beam.

4. An optical computing device as defined in any of paragraphs 1-3, wherein the calibration transfer error correction is determined based upon components of the optical computing device.

5. An optical computing device, comprising electromagnetic radiation that optically interacts with a sample to produce sample-interacted light; a first Integrated Computational Element ("ICE") core positioned to optically interact with the sample-interacted light to thereby generate a first electromagnetic beam which corresponds to a characteristic of the sample; a second ICE core positioned in parallel with the first ICE core to optically interact with the sample-interacted light to thereby generate a second electromagnetic beam which also corresponds to the characteristic of the sample; and a first detector positioned in series with the first ICE core to receive the first electromagnetic beam and thereby generate a first signal utilized to determine the characteristic of the sample; and a second detector positioned in series with the second ICE core to receive the second electromagnetic beam and thereby generate a second signal utilized to determine the characteristic of the sample, wherein one of the first or second signals is utilized to apply a calibration transfer error correction to the other signal.

6. An optical computing device as defined in paragraph 5, wherein the first and second ICE cores have different spectral profiles.

7. An optical computing device as defined in any of paragraphs 5-6, wherein the calibration transfer error correction is determined based upon components of the optical computing device.

8. An optical computing device as defined in any of paragraphs 5-7, further comprising a correction circuit positioned to receive the first and second signals, and thereby utilize one of the first or second signals to apply the calibration transfer error correction to the other signal.

9. An optical computing device as defined in any of paragraphs 5-8, further comprising a computer processor positioned to receive the first and second signals, and thereby utilize one of the first or second signals to apply the calibration transfer error correction to the other signal.

10. A method utilizing an optical computing device, comprising optically interacting electromagnetic radiation with a sample to produce sample-interacted light; optically interacting the sample-interacted light with a first Integrated Computational Element ("ICE") core to produce a first electromagnetic beam; optically interacting the first electromagnetic beam with a second ICE core positioned in series with the first ICE core to thereby produce a second electromagnetic beam; optically interacting the second electromagnetic beam with a detector positioned in series with the first and second ICE cores to thereby generate a signal; and utilizing the signal to determine a characteristic of the sample.

11. A method as defined in paragraph 10, wherein the first and second ICE cores have different spectral profiles.

12. A method as defined in any of paragraphs 10-11, further comprising utilizing the first or second ICE cores to apply a calibration transfer error correction to the second electromagnetic beam.

13. A method as defined in any of paragraphs 10-12, wherein the calibration transfer error correction is achieved using the method comprising calculating a calibration transfer error for the optical computing device based on components of the optical computing device; and utilizing the calibration transfer error to design the first or second ICE cores to correct for the calibration transfer error, thus resulting in the calibration transfer error correction.

14. A method utilizing an optical computing device, comprising optically interacting electromagnetic radiation with a sample to produce sample-interacted light; optically interacting the sample-interacted light with a first Integrated Computational Element ("ICE") core to thereby generate a first electromagnetic beam; optically interacting the sample-interacted light with a second ICE core to thereby generate a second electromagnetic beam; optically interacting the first electromagnetic beam with a first detector to thereby generate a first signal; optically interacting the second electromagnetic beam with a second detector to thereby generate a second signal; utilizing one of the first or second signals to apply a calibration transfer error correction to the other signal; and utilizing the first and second signals to determine a characteristic of the sample.

15. A method as defined in paragraph 14, wherein the first and second ICE cores have different spectral profiles.

16. A method as defined in any of paragraphs 14-15, wherein the calibration transfer error correction is achieved using the method comprising calculating a calibration transfer error for the optical computing device based on components of the optical computing device; and utilizing the calibration transfer error to design the first or second ICE cores to produce an electromagnetic beam used to correct for the calibration transfer error, thus resulting in the calibration transfer error correction.

17. A method as defined in any of paragraphs 14-16, wherein utilizing one of the first or second signals to apply the calibration transfer error correction to the other signal comprises transmitting the first and second signals to a correction circuit; and utilizing the correction circuit to apply the calibration transfer error correction to the other signal.

18. A method as defined in any of paragraphs 14-17, wherein utilizing one of the first or second signals to apply the calibration transfer error correction to the other signal comprises transmitting the first and second signals to a computer processor; and utilizing the computer processor to apply the calibration transfer error correction to the other signal.

19. An optical computing method, comprising calculating a calibration transfer error for an optical computing device based on components of the optical computing device; utilizing the calibration transfer error to determine a calibration transfer error correction; and utilizing the calibration transfer error correction to generate a signal in the optical computing device which corresponds to a characteristic of a sample being analyzed by the optical computing device.

20. A method as defined in paragraph 19, wherein utilizing the calibration transfer error correction to generate the signal comprises providing a first and second Integrated Computational Element ("ICE") core in the optical computing device; and utilizing one of the ICE cores to apply the calibration transfer error correction.

21. A method as defined in any of paragraphs 19-20, wherein utilizing the calibration transfer error correction to generate the signal comprises applying the calibration transfer error correction using a correction circuit.

22. A method as defined in any of paragraphs 19-21, wherein utilizing the calibration transfer error correction to generate the signal comprises applying the calibration transfer error correction using a computer processor.

23. A method to fabricate an optical computing device, comprising calculating a calibration transfer error for an optical computing device based on components of the optical computing device; utilizing the calibration transfer error to determine an optical spectral profile necessary to correct for the calibration transfer error; and designing a first Integrated Computational Element ("ICE") core which corresponds to a characteristic of a sample being analyzed by the optical computing device.

24. A method as defined in paragraph 23, further comprising positioning the first ICE core in series with a second ICE core such that the first ICE core corrects the calibration transfer error present within an output beam of the second ICE core.

25. A method as defined in any of paragraphs 23-24, further comprising positioning the first ICE core in parallel with a second ICE core; positioning a first detector in series with the first ICE core; and positioning a second detector in series with the second ICE core, wherein an output signal of the first detector is utilized to correct for the calibration transfer error present within an output signal of the second detector.

26. A method as defined in any of paragraphs 23-25, further comprising positioning a correction circuit in series with the first and second detectors to thereby correct the calibration transfer error using the output signal of the first detector.

27. A method as defined in any of paragraphs 23-26, further comprising positioning a computer processor in series with the first and second detectors to thereby correct the calibration transfer error using the output signal of the first detector.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. An optical computing device, comprising:
   electromagnetic radiation that optically interacts with a sample to produce sample-interacted light;
   a first Integrated Computational Element ("ICE") core;
   a second ICE core positioned in series with the first ICE core; and
   a detector positioned in series with the first and second ICE cores to receive an electromagnetic beam which has passed through the first and second ICE cores, the detector thereby generates a signal utilized to determine a characteristic of the sample,
   wherein the first or second ICE core is positioned to apply a calibration transfer error correction to the electromagnetic beam.

2. An optical computing device as defined in claim 1, wherein the first and second ICE cores have different spectral profiles.

3. An optical computing device as defined in claim 1, wherein the calibration transfer error correction is determined based upon components of the optical computing device.

4. An optical computing device, comprising:
   electromagnetic radiation that optically interacts with a sample to produce sample-interacted light;
   a first Integrated Computational Element ("ICE") core positioned to optically interact with the sample-interacted light to thereby generate a first electromagnetic beam which corresponds to a characteristic of the sample;

a second ICE core positioned in parallel with the first ICE core to optically interact with the sample-interacted light to thereby generate a second electromagnetic beam which also corresponds to the characteristic of the sample;

a first detector positioned in series with the first ICE core to receive the first electromagnetic beam and thereby generate a first signal utilized to determine the characteristic of the sample; and a second detector positioned in series with the second ICE core to receive the second electromagnetic beam and thereby generate a second signal utilized to determine the characteristic of the sample, wherein one of the first or second signals is utilized to apply a calibration transfer error correction to the other signal.

5. An optical computing device as defined in claim 4, wherein the first and second ICE cores have different spectral profiles.

6. An optical computing device as defined in claim 4, wherein the calibration transfer error correction is determined based upon components of the optical computing device.

7. An optical computing device as defined in claim 4, further comprising a correction circuit positioned to receive the first and second signals, and thereby utilize one of the first or second signals to apply the calibration transfer error correction to the other signal.

8. An optical computing device as defined in claim 4, further comprising a computer processor positioned to receive the first and second signals, and thereby utilize one of the first or second signals to apply the calibration transfer error correction to the other signal.

9. A method utilizing an optical computing device, comprising:

optically interacting electromagnetic radiation with a sample to produce sample-interacted light;

optically interacting the sample-interacted light with a first Integrated Computational Element ("ICE") core to produce a first electromagnetic beam;

optically interacting the first electromagnetic beam with a second ICE core positioned in series with the first ICE core to thereby produce a second electromagnetic beam;

utilizing the first or second ICE core to apply a calibration transfer error correction to the second electromagnetic beam;

optically interacting the second electromagnetic beam with a detector positioned in series with the first and second ICE cores to thereby generate a signal; and utilizing the signal to determine a characteristic of the sample.

10. A method as defined in claim 9, wherein the first and second ICE cores have different spectral profiles.

11. A method as defined in claim 9, wherein the calibration transfer error correction is achieved using the method comprising:

calculating a calibration transfer error for the optical computing device based on components of the optical computing device; and utilizing the calibration transfer error to design the first or second ICE cores to correct for the calibration transfer error, thus resulting in the calibration transfer error correction.

12. A method utilizing an optical computing device, comprising:

optically interacting electromagnetic radiation with a sample to produce sample-interacted light;

optically interacting the sample-interacted light with a first Integrated Computational Element ("ICE") core to thereby generate a first electromagnetic beam;

optically interacting the sample-interacted light with a second ICE core to thereby generate a second electromagnetic beam;

optically interacting the first electromagnetic beam with a first detector to thereby generate a first signal;

optically interacting the second electromagnetic beam with a second detector to thereby generate a second signal;

utilizing one of the first or second signals to apply a calibration transfer error correction to the other signal; and utilizing the first and second signals to determine a characteristic of the sample.

13. A method as defined in claim 12, wherein the first and second ICE cores have different spectral profiles.

14. A method as defined in claim 12, wherein the calibration transfer error correction is achieved using the method comprising:

calculating a calibration transfer error for the optical computing device based on components of the optical computing device; and utilizing the calibration transfer error to design the first or second ICE cores to produce an electromagnetic beam used to correct for the calibration transfer error, thus resulting in the calibration transfer error correction.

15. A method as defined in claim 12, wherein utilizing one of the first or second signals to apply the calibration transfer error correction to the other signal comprises:

transmitting the first and second signals to a correction circuit; and utilizing the correction circuit to apply the calibration transfer error correction to the other signal.

16. A method as defined in claim 12, wherein utilizing one of the first or second signals to apply the calibration transfer error correction to the other signal comprises:

transmitting the first and second signals to a computer processor; and utilizing the computer processor to apply the calibration transfer error correction to the other signal.

17. An optical computing method, comprising:

calculating a calibration transfer error for an optical computing device based on components of the optical computing device;

utilizing the calibration transfer error to determine a calibration transfer error correction; and utilizing a first or second Integrated Computational Element ("ICE") core of the optical computing device to apply the calibration transfer error correction, thereby generating a signal in the optical computing device which corresponds to a characteristic of a sample being analyzed by the optical computing device.

18. A method as defined in claim 17, wherein applying the calibration transfer error correction further comprises applying the calibration transfer error correction using a correction circuit.

19. A method as defined in claim 17, wherein applying the calibration transfer error correction further comprises applying the calibration transfer error correction using a computer processor.

20. A method to fabricate an optical computing device, comprising:

calculating a calibration transfer error for an optical computing device based on components of the optical computing device;

utilizing the calibration transfer error to determine an optical spectral profile necessary to correct for the calibration transfer error; and designing a first Integrated Computational Element ("ICE") core which corresponds to a characteristic of a sample being analyzed by the optical computing device.

21. A method as defined in claim 20, further comprising positioning the first ICE core in series with a second ICE core such that the first ICE core corrects the calibration transfer error present within an output beam of the second ICE core.

22. A method as defined in claim 20, further comprising:

positioning the first ICE core in parallel with a second ICE core;

positioning a first detector in series with the first ICE core; and positioning a second detector in series with the second ICE core, wherein an output signal of the first detector is utilized to correct for the calibration transfer error present within an output signal of the second detector.

23. A method as defined in claim 22, further comprising positioning a correction circuit in series with the first and second detectors to thereby correct the calibration transfer error using the output signal of the first detector.

24. A method as defined in claim 22, further comprising positioning a computer processor in series with the first and second detectors to thereby correct the calibration transfer error using the output signal of the first detector.

* * * * *